(12) United States Patent
Kienle et al.

(10) Patent No.: US 8,355,929 B2
(45) Date of Patent: Jan. 15, 2013

(54) METHODS AND SYSTEMS FOR STORING MEDICAL SUPPLIES

(75) Inventors: Patricia Kienle, Laflin, PA (US); Cynthia Yamaga, Oceanside, CA (US); Thomas Utech, San Diego, CA (US); Mary Zeringue, San Diego, CA (US); Jonathan Zimmerman, San Diego, CA (US); Alisa Goetz, Bellaire, TX (US)

(73) Assignee: CareFusion 303, Inc., San Diego, CA (US)

(*) Notice: Subject to any disclaimer, the term of this patent is extended or adjusted under 35 U.S.C. 154(b) by 340 days.

(21) Appl. No.: 12/400,908

(22) Filed: Mar. 10, 2009

(65) Prior Publication Data

US 2010/0235179 A1    Sep. 16, 2010

(51) Int. Cl.
*G06Q 50/00* (2012.01)
(52) U.S. Cl. .............................. 705/3; 705/2; 340/825.49
(58) Field of Classification Search .................. 705/2, 3; 340/572, 825; 312/209
See application file for complete search history.

(56) References Cited

U.S. PATENT DOCUMENTS

| | | | | |
|---|---|---|---|---|
| 6,021,392 | A * | 2/2000 | Lester et al. ...................... | 705/2 |
| 6,604,019 | B2 * | 8/2003 | Ahlin et al. .................... | 700/231 |
| 7,467,093 | B1 * | 12/2008 | Newton et al. .................... | 705/3 |
| 7,685,026 | B1 * | 3/2010 | McGrady et al. ................ | 705/28 |
| 2005/0236940 | A1 * | 10/2005 | Rockoff .......................... | 312/209 |
| 2008/0316045 | A1 * | 12/2008 | Sriharto et al. ........... | 340/825.49 |
| 2008/0319789 | A1 * | 12/2008 | Vahlberg et al. .................. | 705/2 |
| 2009/0267772 | A1 * | 10/2009 | Dehnadi ..................... | 340/572.8 |

OTHER PUBLICATIONS

CE Today for Pharmacists—Dec. 2000.*

* cited by examiner

*Primary Examiner* — Gerald J. O'Connor
*Assistant Examiner* — Jonathan K Ng
(74) *Attorney, Agent, or Firm* — McDermott Will & Emery LLP (57) ABSTRACT

Storing of medical supplies is performed according to rules promoting safety and ergonomics. The physical arrangement of medical supplies within a storage unit is analyzed. An inventory of medical supplies to be stored in the storage unit is established. A new physical arrangement of medical supplies within the storage unit is determined based on the rules for storing medical supplies and the inventory. The storage unit is configured according to the new physical arrangement. The physical locations within the storage unit where each of the medical supplies is to be stored are indicated. The medical supplies are stored in the indicated locations.

27 Claims, 7 Drawing Sheets

METHODS AND SYSTEMS FOR STORING MEDICAL SUPPLIES

TECHNICAL FIELD

The present disclosure relates to the storing of medical supplies according to rules, such as those promoting safety and ergonomics.

BACKGROUND

The storage of drugs and other medical supplies has become a growing concern for hospitals, suppliers, health care providers and patients. Errors by hospital personnel in the dispensing of drugs can cause serious injury to patients. Some of these errors may be reduced by storing drugs and other medical supplies in a safe and ergonomic manner.

Typically, health care providers, such as hospitals, have an internal pharmacy that co-ordinates the dispensing of drugs to patients. These pharmacies have long been burdened with the increasingly complex inventory management that results from caring for hundreds of patients every day. The responsibilities of an internal pharmacy may include: filling individual patient prescriptions on a daily basis; maintaining sufficient inventory of each drug in the hospital stock to administer to patients on a daily basis; tracking of drug administration to prevent patients from being given drugs that have adverse effects when combined with other drugs; accounting for the purchase of drugs for use in the hospital; accounting associated with the administering of drugs to individual patients; distributing drugs to the appropriate patient care or procedural units within the hospital to suit each unit's daily demands; tracking of drug expiration dates to rid inventories of expired drugs; and tracking of drug lot numbers, for example, in the event of a recall of a particular drug or drug lot number. Hospital and pharmacy functions may be classified to include six critical processes: selection, storage, ordering and transcribing, dispensing, administering and monitoring of medical supplies.

In recent years, hospitals have been assisted with drug distribution management by the introduction of drug dispensing machines and health care supply dispensing machines. These dispensing machines have effectively created branches of the pharmacy department at each patient care or procedural unit where the dispensing machines are located. The dispensing machines are usually connected to a computer system within the internal pharmacy for tracking drugs that are to be administered to patients in a particular patient care location of the hospital. Hospitals have thus improved the manner in which drugs are dispensed to patients, by having the dispensing machines report (through the computer system) the variety and quantities of drugs and medical supplies being dispensed.

As the automated medication dispensing industry has matured, state regulatory agencies are beginning to address new technologies in the field and require assurance that an item in a section or drawer of a medical supply dispensing machine is exactly what the machine represents it to be. At present, the storage of drugs and other medical supplies in dispensing units is managed on an ad hoc basis by hospital personnel. Dispensing machines are arranged and re-arranged as needed depending on patient requirements, par levels and various other criteria. It is not uncommon for drugs to be packaged in containers which look alike (look-alike drugs), resulting in the incorrect storage of drugs owing to hospital personnel mistakenly placing drugs with similar containers or packaging in the wrong compartments of dispensing machines. These drugs may then be incorrectly retrieved and administered. Hospital personnel may also mistakenly retrieve the wrong drugs, if drugs packaged in similar containers are stored in close proximity in a dispensing machine. The same mistaken storage or mistaken retrieval may be caused by drugs with similar sounding names or names that are spelled similarly (sound-alike drugs).

SUMMARY

There is a need in the art for methods and systems that organize the storage of drugs and medical supplies in a safe and ergonomic manner so as to reduce the likelihood of mistaken storage and retrieval.

One system of the present disclosure comprises a storage unit and an inventory of medical supplies to be stored in the storage unit, and functions as follows. An organizational unit of the system determines a physical arrangement of the inventory of medical supplies within the storage unit according to rules for storing medical supplies. The rules are stored in a database. An indicator of the system indicates physical locations within the storage unit where medical supplies are to be stored based on the determined physical arrangement.

Additional features and advantages of the disclosure will be set forth in the description below, and in part will be apparent from the description, or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure. In the drawings.

DETAILED DESCRIPTION

It is contemplated that the subject matter described herein may be embodied in many forms. Accordingly, the embodiments described in detail below are the presently preferred embodiments, and are not to be considered as limitations.

The disclosed embodiments address, among other things, the safe and ergonomic storage of medical supplies. The term "medical supplies" refers to drugs, and other supplies such as syringes, bandages, sponges, tape, vials, among other things. One skilled in the art would appreciate that medical supplies are not limited to the items mentioned, and include any items that may be stored in a health care facility for the purpose of health care.

Figure 1:
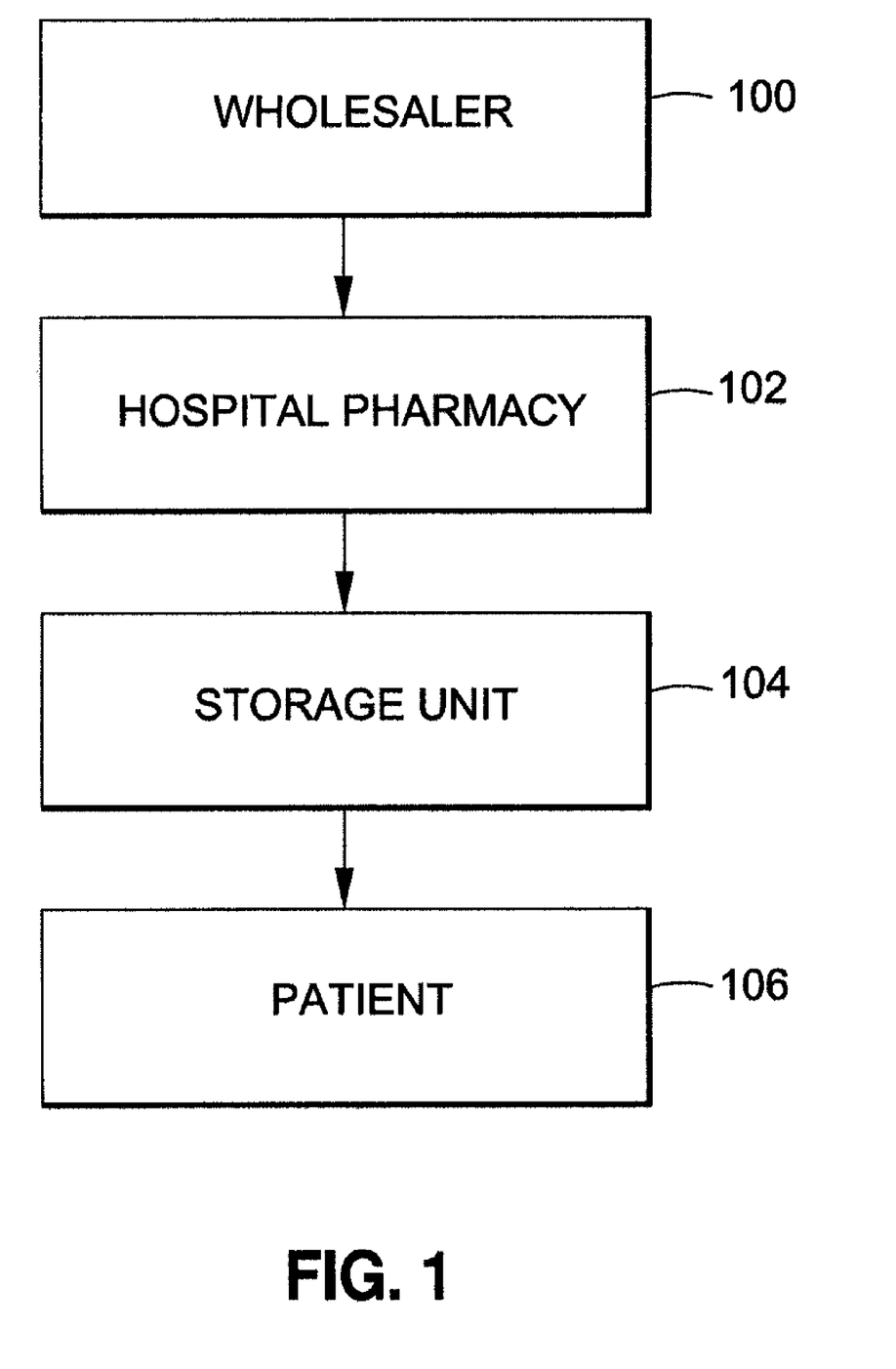
FIG. 1 is a flow chart diagram depicting the path of medical supplies.

FIG. 1 shows the typical path of medical supplies through the health care system. Hospitals (or other health care facilities) purchase medical supplies from a wholesaler 100, which may be the manufacturer, or some other party. The medical supplies are then stored in the hospital pharmacy 102. The supplies remain in the hospital pharmacy 102 until such time as they are needed at patient care or procedural units. When this need arises, the medical supplies are stored in storage units 104 for dispensing to patients 106. Although the present disclosure describes the storage of medical supplies in storage units, the present disclosure is equally applicable to the storage of medical supplies by the wholesaler 100 and the hospital pharmacy.

Figure 2A:
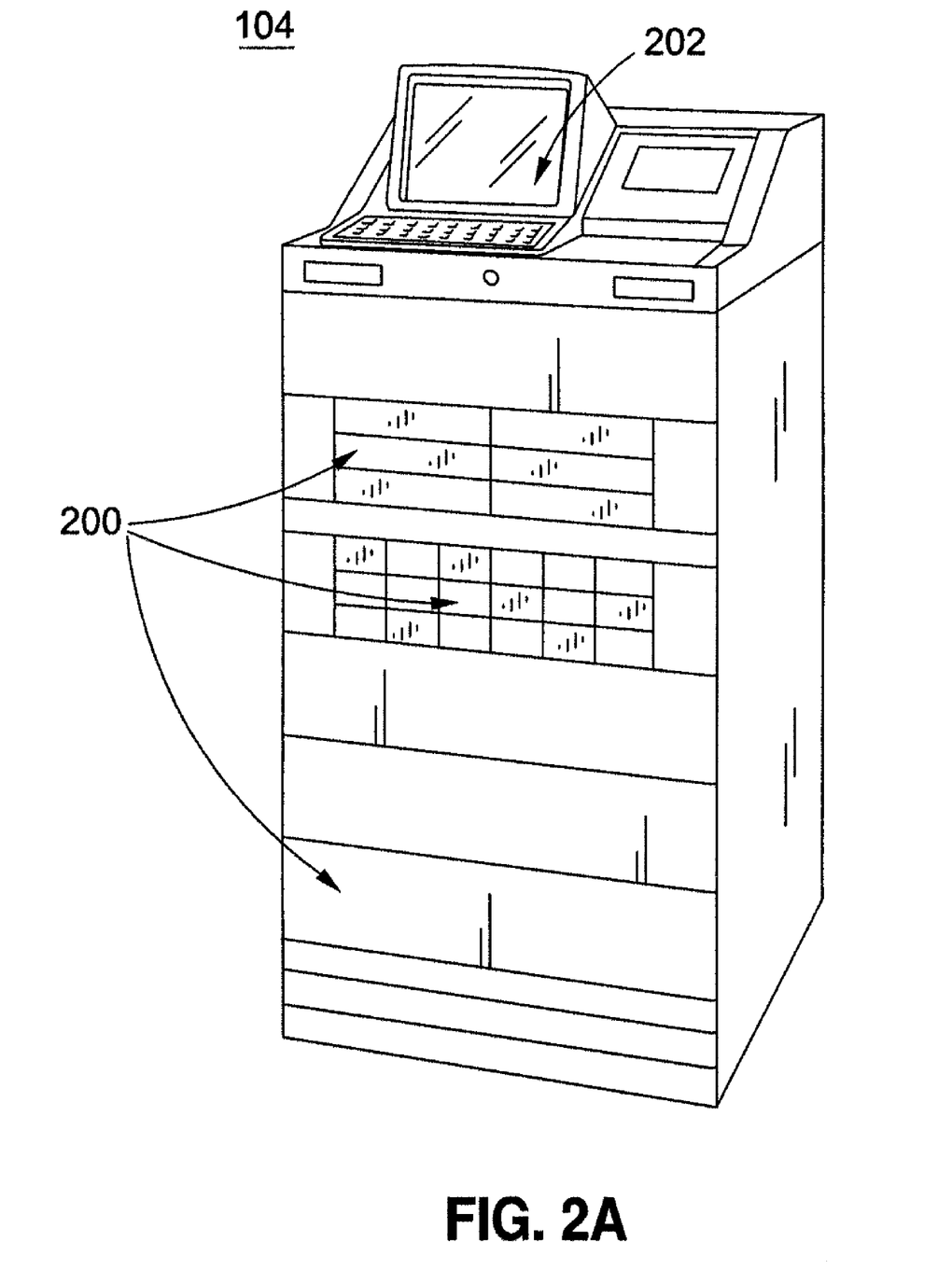
FIG. 2A depicts a storage unit for storing drugs and medical supplies according to certain embodiments of the present disclosure.
Figure 2B:
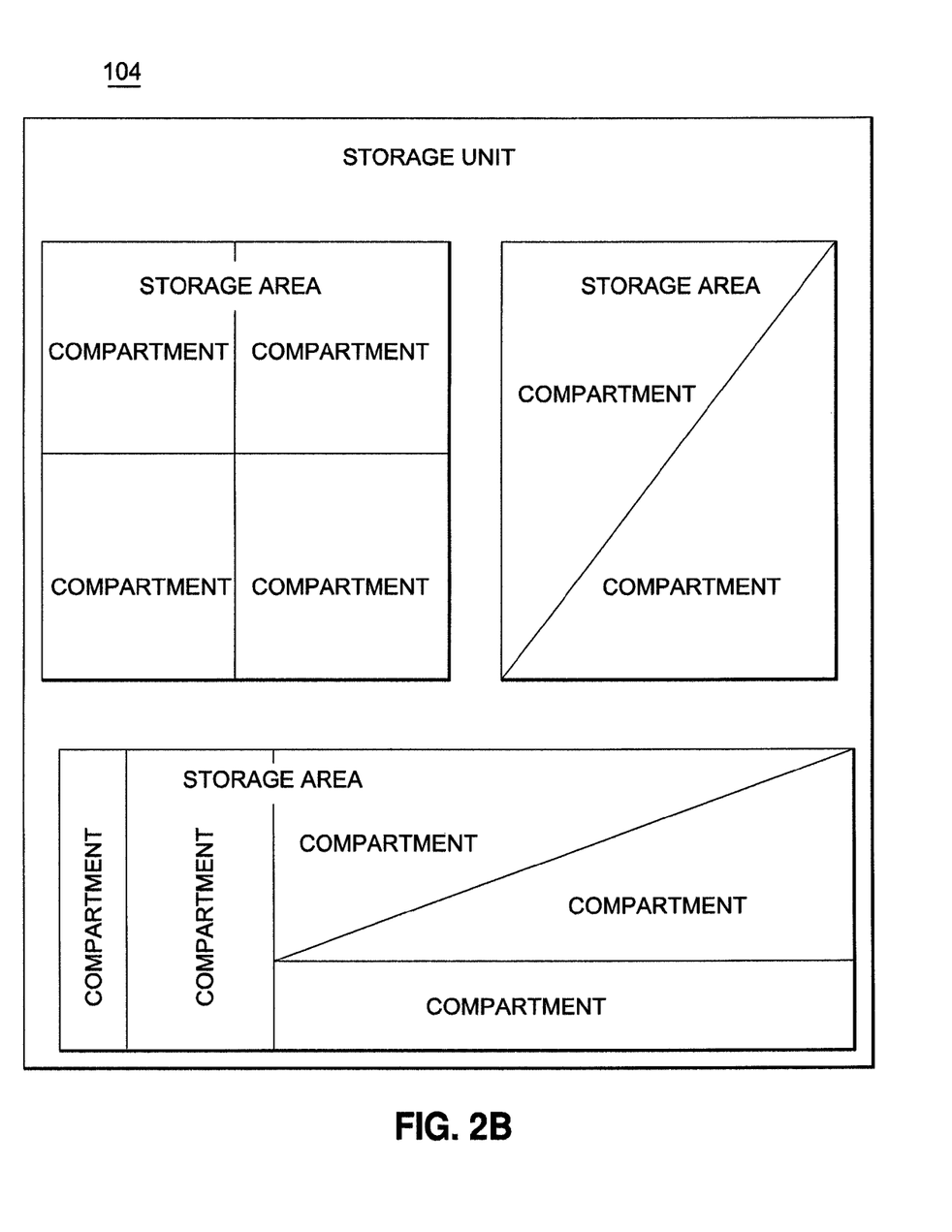
FIG. 2B is a block diagram depicting an exemplary organization of a storage unit.
Figure 2C:
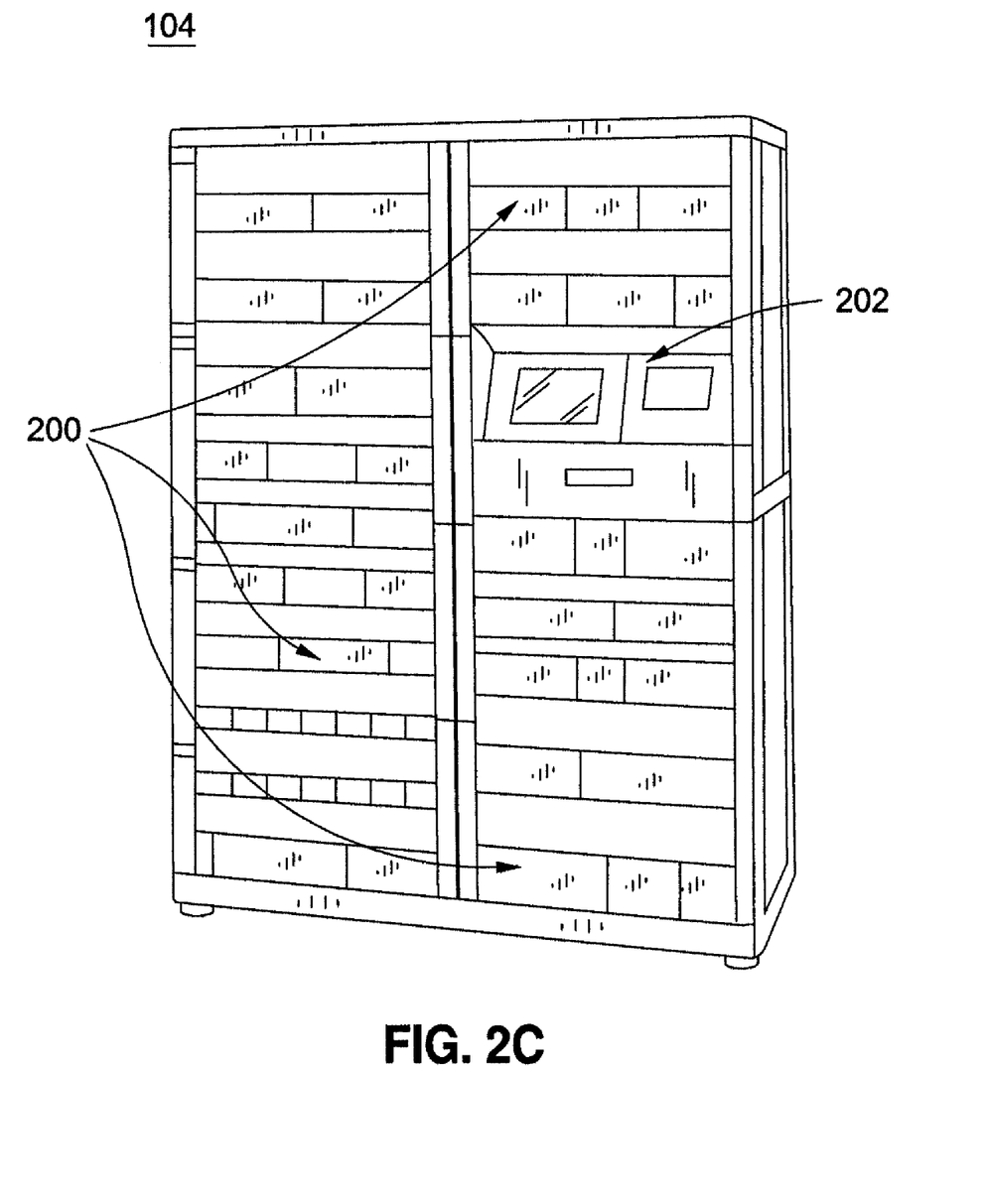
FIG. 2C depicts a storage unit for storing drugs and medical supplies according to certain embodiments of the present disclosure.

FIG. 2A shows one embodiment of a storage unit 104. A storage unit 104 may be a MedStation™ (as shown in FIGS. 2A and 2C), a cabinet, a drawer, a cupboard, a shelf, a set of shelves, a box, a bin or a closet, among other things. Storage units 104 will typically be located at patient care or procedural units of a hospital (or other health care facility). A storage unit 104 comprises one or more storage areas (see FIG. 2B) in which medical supplies are stored. The storage unit 104 shown in FIG. 2A has several drawers 200 for storing medical supplies. Examples of how drawers may be arranged are shown in FIG. 3.

Figure 3A:
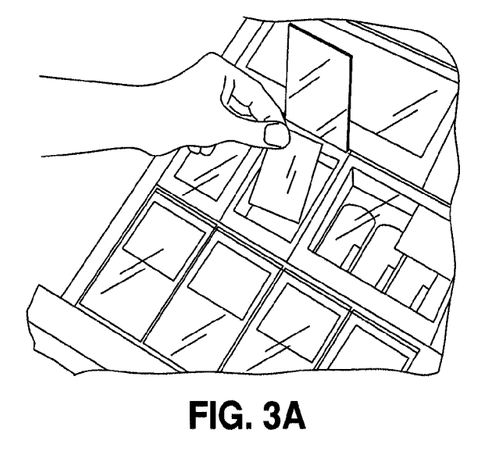
FIGS. 3A-3C depict an exemplary organization of drawers of a storage unit according to certain embodiments of the present disclosure.
Figure 3B:
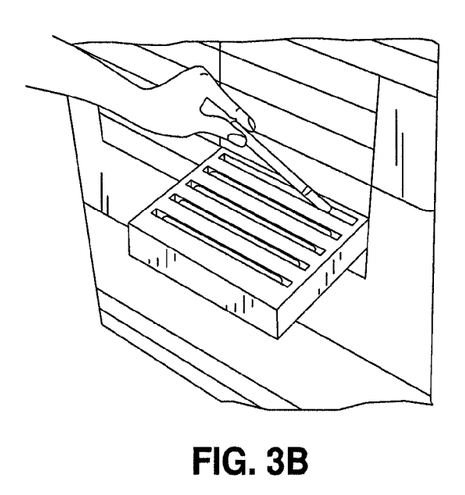
Figure 3C:
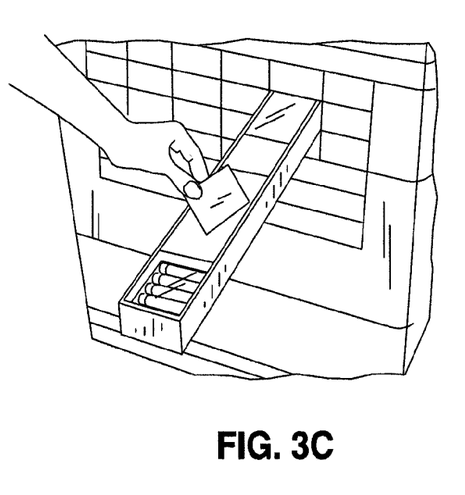

Storage areas in storage units 104, such as the drawers 200, can themselves be divided into compartments, as shown in FIGS. 3A-3C, which depict examples of drawers 200 divided into compartments. FIG. 2B shows a logical breakdown of a storage unit into storage areas and of storage areas into compartments. A storage area may be divided into compartments by dividers, bins, shelves, or containers such as boxes, vial stands, beakers or bags and the like, among other ways.

FIG. 2C depicts a second embodiment of a storage unit 104. The storage unit 104 in FIG. 2C has a relatively more open setup than the arrangement in FIG. 2A. The open setup in FIG. 2C makes it easier for health care personnel to mistakenly store medical supplies in the wrong compartment/storage area, or mistakenly retrieve medical supplies from the wrong compartment/storage area. Health care personnel are more likely to place medical supplies in the wrong compartment when storing the supplies in one of the drawers 200, owing to the open nature of the drawers 200.

At present, when medical supplies are placed in storage units (such as those shown in FIGS. 2A and 2C) by health care personnel, the supplies are typically stored according to the availability of free space, or alphabetically. Storing medical supplies, especially medications, in this manner is prone to error, as supplies which look alike (look-alike medical supplies) are often stored contiguously, or in close proximity to each other, as are medical supplies with names that sound alike (sound-alike medical supplies).

The present disclosure helps to mitigate a number of concerns. One of these is "mistaken misplacement." This concern refers to health care personnel mistakenly placing medical supplies in the incorrect compartment or storage area within a storage unit, for reasons of proximity, lack of attention, look-alike or sound-alike characteristics of the medical supplies, some combination of these factors, or other reasons.

Another concern is that of "mistaken retrieval." This concern refers to health care personnel mistakenly retrieving medical supplies from the incorrect compartment or storage area within a storage unit (and hence retrieving the wrong supplies), for reasons of proximity, lack of attention, look-alike or sound-alike characteristics of the supplies, some combination of these factors, or other reasons.

Another concern is that of "mistaken retrieval caused by mistaken placement." This refers to health care personnel mistakenly retrieving the wrong medical supplies from the correct compartment or storage area within a storage unit, because the supplies were incorrectly placed there for storage owing to proximity, lack of attention, look-alike or sound-alike characteristics of the supplies, some combination of these factors, or other reasons.

In certain preferred embodiments, a storage unit is linked to a computer system 202. The computer system 202 may be located on the storage unit 104 itself, as shown in FIGS. 2A and 2C, in another room or at a remote location. The computer system 202 may be a PAR$_X$® system, a Pyxis® system, a computer connected to a PAR$_X$® system and/or a Pyxis® system, among other exemplary systems. The computer system 202 has many functions, three of which are to keep track of (1) the contents of the storage unit, (2) the physical arrangement of the storage unit and (3) the physical configuration of the storage area(s) comprising the storage unit, i.e., the layout of the compartments within storage areas. Although certain exemplary systems have been named, other conventional computer systems can be employed with the present embodiments of the disclosure.

In one embodiment of the present disclosure, when a particular medical supply item needs to be replenished or added to a storage unit, the computer system 202 notifies health care personnel. Whether a medical supply item must be replenished may be determined according to par levels, which are the minimum acceptable levels for medical supplies as set by health care personnel. Replenishment may also be determined based on the patient base. If a new patient is admitted, who is in need of particular medical supplies, the par levels for those medical supplies in the storage unit designated to serve the patient may need to be increased. Alternatively, a patient who is already being serviced by a particular storage unit, may receive a new diagnosis, causing a change in the medical supplies that need to be stored in the assigned storage unit 104. Once the computer system 202 becomes aware of changes to the medical supplies that are required to be stored in the storage unit 104, the computer system 202 can determine whether the medical supplies in the storage unit 104 need to be added to, replenished or replaced.

Figure 4:
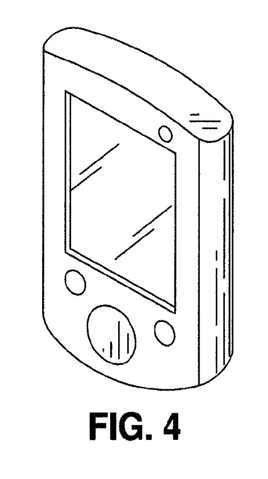
FIG. 4 depicts a hand-held device according to certain embodiments of the present disclosure.

In certain preferred embodiments, the medical supplies are provided with a bar code or other scannable or machine-readable identifier. When health care personnel wish to add medical supplies to a storage unit 104, the bar code or other identifier of the item to be added must first be scanned into the computer system 202. Alternatively, the item can be scanned into a hand-held device (see FIG. 4) that is capable of communicating with the computer system 202. The computer system 202 then indicates where within the storage unit 104 the item is to be safely stored. In the embodiment shown in FIGS. 2A-2C and 3A-3C, the computer system 202 indicates the proper storage location by ejecting the correct drawer 200 in which the item is to be stored. Alternatively, the proper storage location may be indicated by the hand-held device, for example, on a digital screen of the hand-held device. Other indications may be used, including signal lights, audio and tactile.

Figure 5:
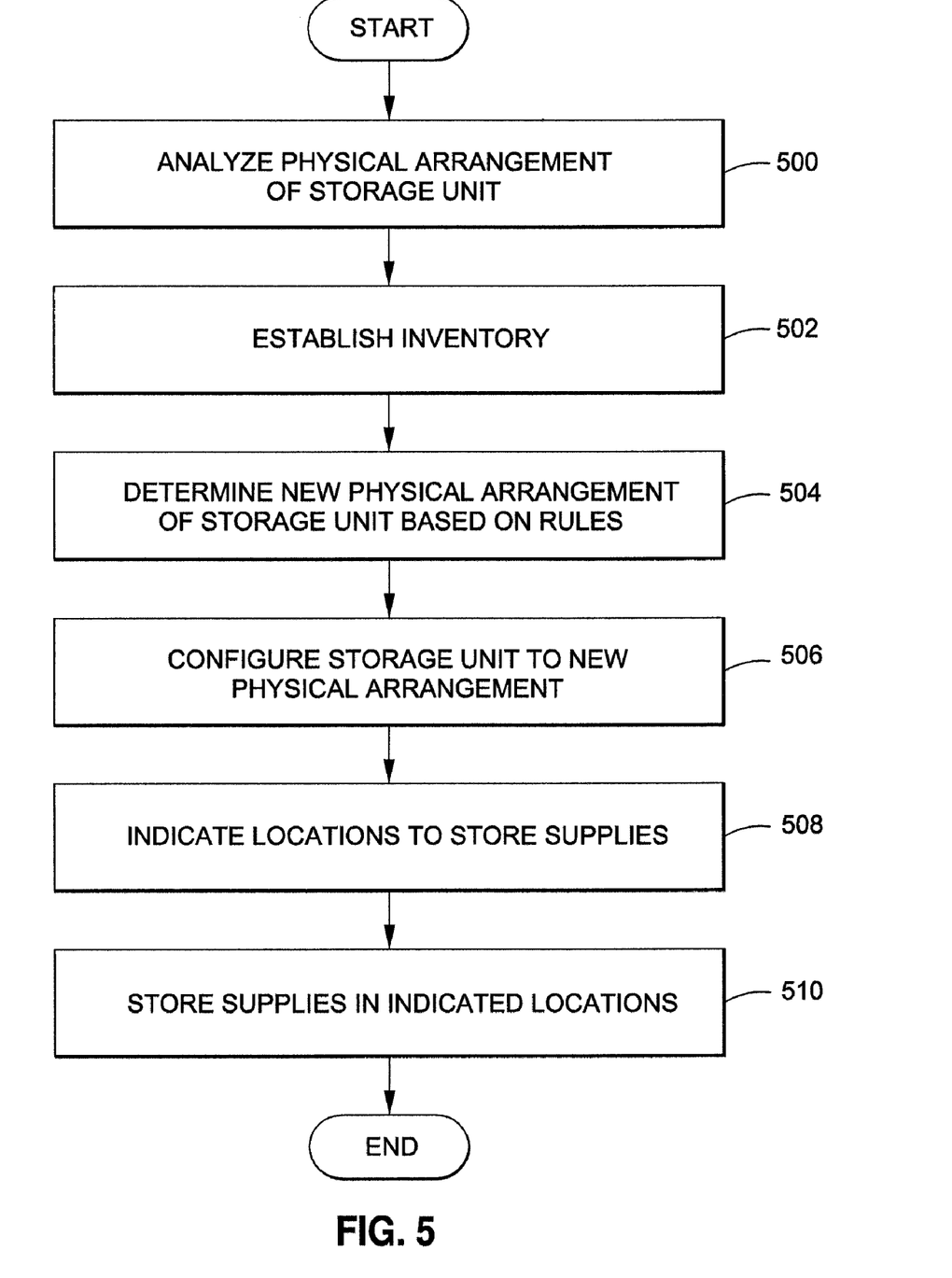
FIG. 5 is a flow chart diagram depicting a method for storing drugs according to certain embodiments of the present disclosure.
Figure 6:
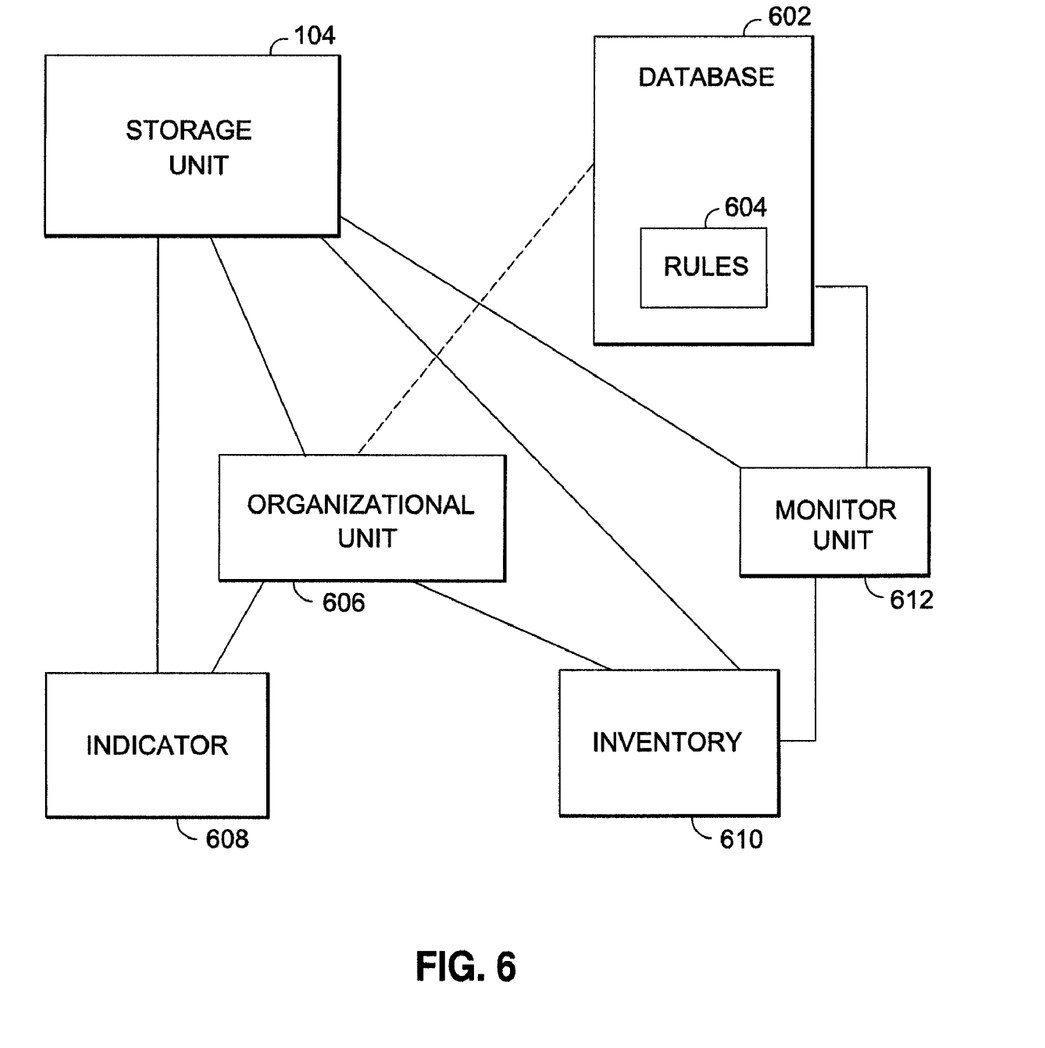
FIG. 6 is a block diagram depicting a system for storing drugs according to certain embodiments of the present disclosure.

FIG. 5 depicts an exemplary method, and FIG. 6 depicts an exemplary architecture for performing the disclosed methods, which may be realized by a computer, a personal digital assistant, a networked computer, or any other suitable processing device or combination thereof. The method in FIG. 5 is executed whenever the contents of a storage unit are to be modified. The method for storing medical supplies in FIG. 5 begins once the supplies have been scanned into the computer system 202.

The first step 500 analyzes the current physical arrangement of medical supplies within the storage unit 104. Step 500 is performed by the organizational unit 606, and involves determining one or more of the following, among other things: (1) the overall size and capacity of the storage unit 104, (2) how many storage areas the storage unit 104 contains, (3) the size and capacity of each storage area, (4) the physical configuration of the storage areas within the storage unit 104, including their relative locations, (5) the physical arrangement of each storage area, which includes the shape of the area, the dimensions of the area and the configuration of any compartments into which the storage area is divided. This information may be entered by health care personnel, stored on a hard drive, server or database (such as database 602), obtained though a network, or acquired some other way.

The second step 502 determines the inventory of medical supplies currently stored in the storage unit 104, as well as the medical supplies that are about to be added to the storage unit 104. This information may be scanned or manually entered into the system of FIG. 6 by health care personnel, stored on a hard drive, server or database (such as database 602), obtained though a network, or acquired in some other manner.

Step 504 determines a new physical arrangement of medical supplies within the storage unit 104. This step of determining is based on a set of rules 604 for storing medical supplies safely and ergonomically, and is executed by the organizational unit 606. The set of rules 604 may include rules from the guidelines "Safety Formulary for the Safe Storage of Medications" and "The Cardinal Health Integrated Medication Solutions Safety Formulary," among other known sources. The rules 604 are stored on a database 602, which may be a hard drive, server or network, among other things.

Safety Formulary recommendations that may form part of the rules 604, may include:
  Drug Access Advisors: These are recommendations for products,
    Which due to the emergent nature of their use, shall be allowed for override status to provide needed availability to practitioners, and/or
    Which due to their high harm potential shall not be allowed for override status from automated dispensing devices, among other things.
  Drug Warning/Monitoring Advisors: These are recommendations for alerts or information relevant to the drug which may be viewable by different personnel. These recommendations include, among other things, required input from administering personnel (such as clinical data entry for use of identified trigger medications), and/or auto alerts based on product specific monitoring parameters (for example, whether the dose exceeds the maximum dose allowed; lab values that must be confirmed before administering a dose, among other things).
  Drug Naming/Display Advisors: These are recommendations for standard naming/display conventions, such as, Tall Man lettering and the placement of numbers or terms, among other things.

The rules 604 for safe storage may include rules such as requiring look-alike and sound-alike medical supplies to be stored in non-contiguous compartments of a storage area, or in different storage areas of a storage unit 104. A second example of a rule 604 is to require medical supplies with multiple strengths, concentrations or sizes to be stored in non-contiguous compartments of a storage area, or in different storage areas of a storage unit 104. A third example of a rule 604 is to allow or disallow certain medical supplies to be stored in specific compartments, such as open matrix drawers or open shelves, among others, or storage areas. An example of an ergonomic rule 604 is to require that the most frequently used medical supplies be stored in the most easily accessible compartments or storage areas. Other examples of rules 604 include: allowing or disallowing certain medical supplies, doses of medical supplies, concentrations of medical supplies or forms of medical supplies to be stored in specific care areas (such as pediatrics or the neonatal ICU, among others); allowing or disallowing certain medical supplies, doses of medical supplies, concentrations of medical supplies or forms of medical supplies to be stored at units according to characteristics of users of units (such as time in practice and/or specialty of practice and/or staff status, among other things); restricting the storage of medical supplies in particular compartments or areas based on characteristics of the medical supplies themselves, such as whether a drug is characterized as Pregnancy Category X or is designated as a hazardous chemical, among other things; displaying warning to the user based determinations using several factors, such as the application of a modified "Harm Index," the existence of multiple strengths, concentrations, and/or dosage forms of a medical supply in the same storage area, user characteristics and population served, among other things. These are but a few examples of rules 604 that may be employed. The programming and setting of rules 604 may be readily performed by one of skill in the art of programming.

Step 504 determines a new physical arrangement of a storage unit 104, such that the inventory 610 of the storage unit 104, as well as any medical supplies being added to the storage unit 104 can be stored in accordance with the rules 604 for storing medical supplies safely and ergonomically. The new physical arrangement of a storage unit 104 may not require any changes to the current physical arrangement, or it may require that the entire storage unit be re-arranged. This step is executed by the organizational unit 606.

When a storage unit 104 is to be re-arranged, the new physical arrangement may not only require that medical supplies be removed from their current compartments and placed in other compartments, but also that the actual layout of compartments within storage areas be modified. For example, a new physical arrangement may require that a storage area containing four compartments be re-arranged to contain only two compartments, or vice versa. This can be readily achieved, for example, by moving, removing or adding partitions within a storage area.

In addition, a new physical arrangement of a storage area may require that the layout of the storage areas within a storage unit 104 be modified. For example, a storage unit 104 with shelves as storage areas may require shelf heights or depths to be modified.

Step 506 configures the storage unit 104 according to the new physical arrangement. This involves modifying the layout of the storage areas and the compartments in the storage areas to follow the new physical arrangement determined in step 504. Health care personnel may execute this step by making the necessary changes to the storage unit 104, or it may be performed automatically by an automated system.

Step 508 employs a system of the present invention (such as the system shown in FIG. 6) that indicates to health care personnel where to store medical supplies in the storage unit 104, according to the new physical arrangement of the storage unit 104. This step is performed by the indicator 608, for each of the medical supplies being stored in the storage unit 104. The indicator 608 indicates the proper location in the storage unit 104 for storage of medical supplies to medical personnel visually (using a light, display screen, or some other visual device) or by sound (using any sound emitting device). Health care personnel then store the medical supplies in the compartments or storage areas of the storage unit 104 indicated by the indicator 608. This step is shown as step 510 in FIG. 5, and completes a method of the present disclosure.

One embodiment of the present disclosure checks for correct placement of medical supplies in the storage unit 104. Upon storage of medical supplies, the indicator 608 confirms correct placement of medical supplies inside the storage unit 104, or alerts medical personnel that the medical supplies have not been stored in the correct area or compartment of the storage unit 104. If medical supplies are incorrectly stored, medical personnel are then able to correct the placement of the medical supplies. The indicator 608 indicates correct or incorrect placement of medical supplies to medical personnel visually (using a light, display screen, or some other visual device) or by sound (using any sound emitting device).

The system in FIG. 6 also shows a monitor unit 612, which monitors the contents of the storage unit 104. The monitor unit 612 determines when a particular medical supply item needs to be replenished or added to the storage unit 104, so that health care personnel can be notified. An alert unit may then be employed to inform medical personnel that replenishment is necessary. The alert unit can alert medical personnel visually (using a light, display screen, or some other visual device) or by sound (using any sound emitting device). The alert unit may be a separate device from the monitor unit 612, or it may be incorporated in the monitor unit 612.

The description of the invention is provided to enable any person skilled in the art to practice various embodiments described herein. While the present disclosure has been particularly described with references to various figures and embodiments, it should be understood that these are for illustration purposes only and should not be taken as limiting the scope of the disclosure. There may be many other ways to implement the embodiments of the disclosure. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the disclosure.

Those of ordinary skill would further appreciate that the various illustrative logical modules, circuits and algorithms described in connection with the embodiments disclosed herein may be implemented as electronic hardware, computer software or combinations of both. To clearly illustrate this interchangeability of hardware and software, various illustrative components, blocks, modules, circuits and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a filed programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional process, control, microcontroller, or state machine. A process may also be implemented as a combination of computing devices, e.g., a combination of a DSP and a microprocessor, a plurality of microprocessors, one or more microprocessors in conjunction with a DSP core, or any other such configuration.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the disclosure. Thus, the present disclosure is not intended to be limited to the aspects shown herein but is to be accorded the widest scope consistent with the principles and novel features disclosed herein.

By employing the disclosed systems and methods, the incidents of incorrect storage and retrieval of medical supplies will be reduced or eliminated. This has the benefits of reducing the risks of harm to patients, loss of inventory, as well as improving ergonomics for health care workers.

What is claimed is:

1. A system for storing medical supplies comprising:
a storage unit comprising a plurality of compartments configured to store medical supplies;

a database configured to store physical location rules specific to storing medical supplies among the plurality of compartments so as to reduce a likelihood of at least one of incorrectly storing and incorrectly retrieving the medical supplies among the plurality of compartments, wherein the physical location rules comprise at least one of:
- storing, in non-contiguous compartments from among the plurality of compartments or different areas of the storage unit, at least one of: look-alike medical supplies, sound-alike medical supplies, a medical supply with multiple strengths, a medical supply with multiple concentrations, or a medical supply with multiple sizes; and
- restricting a specific medical supply to storage in a subset of the plurality of compartments;

an organizational unit configured to:
- analyze a current physical location arrangement of medical supplies among the plurality of compartments of the storage unit;
- determine a new physical location arrangement of the medical supplies within the plurality of compartments of the storage unit based on the rules specific to storing medical supplies; and
- provide a warning for display based on at least one of a harm index, a medical supply having multiple strengths, a medical supply having multiple concentrations, a medical supply having multiple sizes, a look-alike medical supply, a sound-alike medical supply, or a patient characteristic; and an indicator configured to indicate physical locations within the storage unit to store the medical supplies among the plurality of compartments based on the determined physical arrangement.

2. The system of claim 1, further comprising an inventory of medical supplies, wherein the inventory comprises medical supplies already present in the storage unit as well as medical supplies that are to be at least one of added and removed from the storage unit, the organizational unit being further configured to determine the physical arrangement based on the rules for storing medical supplies and the inventory of medical supplies.

3. The system of claim 1, further comprising a monitor configured to monitor the amounts of medical supplies present in the storage unit and configured to alert users of the storage unit when medical supplies must be at least one of replenished and added to the storage unit based on at least one of par levels and updated patient information.

4. The system of claim 1, wherein the organizational unit is configured to determine an ergonomically optimal physical arrangement of medical supplies within the storage unit.

5. The system of claim 1, wherein the organizational unit and the indicator are on a single hand-held device.

6. The system of claim 1, wherein the organizational unit is connected to a second database, the second database storing information regarding the contents of the storage unit.

7. The system of claim 1, wherein the organizational unit and the indicator are on the storage unit.

8. The system of claim 1, wherein the indicator is further configured to confirm correct physical storage of medical supplies in the storage unit according to the determined physical arrangement and to alert users of the storage unit of incorrect physical storage of medical supplies in the storage unit according to the determined physical arrangement.

9. The system of claim 1, further comprising a scanner configured to scan labels on medical supplies to be stored in the storage unit.

10. The system of claim 9, wherein the scanner, the organizational unit and the indicator are on a single hand-held device.

11. The system of claim 1, wherein a physical layout of the plurality of compartments is configured to be modifiable, and wherein the organizational unit being configured to determine the new physical location arrangement of medical supplies within the plurality of compartments of the storage unit comprises the organizational unit being configured to determine whether the physical layout of the plurality of compartments should be modified.

12. A method for storing medical supplies comprising:
- analyzing, using a processor, a current physical location arrangement of medical supplies among a plurality of compartments of a storage unit configured to store medical supplies;
- determining a new physical location arrangement of the medical supplies within the plurality of compartments of the storage unit based on rules specific to storing medical supplies so as to reduce a likelihood of at least one of incorrectly storing and incorrectly retrieving the medical supplies, wherein the rules comprise at least one of:
- storing, in non-contiguous compartments from among the plurality of compartments or different areas of the storage unit, at least one of: look-alike medical supplies, sound-alike medical supplies, a medical supply with multiple strengths, a medical supply with multiple concentrations, or a medical supply with multiple sizes; and
- restricting a specific medical supply to storage in a subset of the plurality of compartments;
- configuring the plurality of compartments of the storage unit according to the step of determining;
- indicating a physical location within at least one plurality of compartments of the storage unit to store each of the medical supplies based on the new physical location arrangement;
- storing each of the medical supplies in the storage unit according to the step of indicating; and
- providing a warning for display based on at least one of a harm index, a medical supply having multiple strengths, a medical supply having multiple concentrations, a medical supply having multiple sizes, a look-alike medical supply, a sound-alike medical supply or a patient characteristic.

13. The method of claim 12, further comprising:
- monitoring the amounts of medical supplies present in the storage unit; and
- alerting users of the storage unit to add medical supplies to the storage unit based on at least one of par levels and updated patient information.

14. The method of claim 12, wherein the new physical arrangement is an ergonomically optimal physical arrangement of medical supplies within the storage unit.

15. The method of claim 12, further comprising scanning labels on medical supplies to be stored in the storage unit.

16. The method of claim 12, further comprising confirming correct physical storage of medical supplies in the storage unit according to the determined physical arrangement and alerting users of the storage unit of incorrect physical storage of medical supplies in the storage unit according to the determined physical arrangement.

17. The method of claim 12, further comprising establishing an inventory of medical supplies to be stored in the storage unit, wherein the inventory comprises medical supplies already present in the storage unit as well as medical supplies that are to be at least one of added to and removed from the storage unit, and wherein the determining of the new physical arrangement is further based on the inventory.

18. The method of claim 17, wherein the establishing comprises checking a database which stores information regarding the contents of the storage unit.

19. The method of claim 12, wherein a physical layout of the plurality of compartments is configured to be modifiable, and wherein the determining the new physical location arrangement of medical supplies within the plurality of compartments of the storage unit comprises determining whether the physical layout of the plurality of compartments should be modified.

20. A non-transitory computer-readable medium storing instructions thereon causing a computer to execute a method comprising:
   analyzing a current physical location arrangement of medical supplies among a plurality of compartments of a storage unit configured to store medical supplies;
   determining a new physical location arrangement of the medical supplies within the plurality of compartments of the storage unit based on rules specific to storing medical supplies so as to reduce a likelihood of at least one of incorrectly storing and incorrectly retrieving the medical supplies, wherein the rules comprise at least one of:
      storing, in non-contiguous compartments from among the plurality of compartments or different areas of the storage unit, at least one of: look-alike medical supplies, sound-alike medical supplies, a medical supply with multiple strengths, a medical supply with multiple concentrations, or a medical supply with multiple sizes; and
      restricting a specific medical supply to storage in a subset of the plurality of compartments;
   configuring the plurality of compartments of the storage unit according to the step of determining;
   indicating a physical location within at least one plurality of compartments of the storage unit to store each of the medical supplies based on the new physical location arrangement;
   storing each of the medical supplies in the storage unit according to the step of indicating; and
   providing a warning for display based on at least one of a harm index, a medical supply having multiple strengths, a medical supply having multiple concentrations, a medical supply having multiple sizes, a look-alike medical supply, a sound-alike medical supply, or a patient characteristic.

21. The computer-readable medium of claim 20, the method further comprising:
   monitoring the amounts of medical supplies present in the storage unit; and alerting users of the storage unit to add medical supplies to the storage unit based on at least one of par levels and updated patient information.

22. The computer-readable medium of claim 20, wherein the new physical arrangement is an ergonomically optimal physical arrangement of medical supplies within the storage unit.

23. The computer-readable medium of claim 20, the method further comprising scanning labels on medical supplies to be stored in the storage unit.

24. The computer-readable medium of claim 20, the method further comprising confirming correct physical storage of medical supplies in the storage unit according to the determined physical arrangement and alerting users of the storage unit of incorrect physical storage of medical supplies in the storage unit according to the determined physical arrangement.

25. The computer-readable medium of claim 20, the method further comprising establishing an inventory of medical supplies to be stored in the storage unit, wherein the inventory comprises medical supplies already present in the storage unit as well as medical supplies that are to be at least one of added to and removed from the storage unit, and wherein the determining of the new physical arrangement is further based on the inventory.

26. The computer-readable medium of claim 25, wherein the establishing comprises checking a database which stores information regarding the contents of the storage unit.

27. The computer-readable medium of claim 20, wherein a physical layout of the plurality of compartments is configured to be modifiable, and wherein the determining the new physical location arrangement of medical supplies within the plurality of compartments of the storage unit comprises determining whether the physical layout of the plurality of compartments should be modified.

* * * * *